(12) United States Patent
Harn et al.

(10) Patent No.: US 10,987,339 B2
(45) Date of Patent: Apr. 27, 2021

(54) USES OF BUTYLIDENEPHTHALIDE

(71) Applicant: EVERFRONT BIOTECH INC., New Taipei (TW)

(72) Inventors: Horng-Jyh Harn, New Taipei (TW); Tzyy-Wen Chiou, New Taipei (TW); Shinn-Zong Lin, New Taipei (TW); Ssu-Yin Yen, New Taipei (TW)

(73) Assignee: EVERFRONT BIOTECH INC., New Tapei (TW)

( * ) Notice: Subject to any disclaimer, the term of this patent is extended or adjusted under 35 U.S.C. 154(b) by 31 days.

(21) Appl. No.: 16/025,764

(22) Filed: Jul. 2, 2018

(65) Prior Publication Data

US 2018/0311208 A1 Nov. 1, 2018

Related U.S. Application Data

(63) Continuation-in-part of application No. 15/232,262, filed on Aug. 9, 2016, now abandoned.

(60) Provisional application No. 62/207,226, filed on Aug. 19, 2015.

(30) Foreign Application Priority Data

Jun. 3, 2016 (TW) .................................. 105117580

(51) Int. Cl.
*A61K 31/365* (2006.01)
*A23L 33/10* (2016.01)
*A61P 35/02* (2006.01)

(52) U.S. Cl.
CPC ............ *A61K 31/365* (2013.01); *A23L 33/10* (2016.08); *A61P 35/02* (2018.01); *A23V 2002/00* (2013.01); *A23V 2200/30* (2013.01)

(58) Field of Classification Search
CPC ........ A61K 31/365; A23L 33/10; A61P 35/02
USPC ........................................................ 514/470
See application file for complete search history.

(56) References Cited

U.S. PATENT DOCUMENTS

| | | |
|---|---|---|
| 7,455,861 B2 | 11/2008 | Luo et al. |
| 2006/0110469 A1 | 5/2006 | Luo et al. |
| 2007/0134351 A1 | 6/2007 | Luo et al. |
| 2008/0255061 A1 | 10/2008 | Chen et al. |
| 2011/0183015 A1 | 7/2011 | Hsieh et al. |
| 2012/0178803 A1* | 7/2012 | Harn ............... A61K 31/343 514/473 |
| 2013/0158108 A1* | 6/2013 | Chiou ............... A61K 31/343 514/470 |
| 2014/0212970 A1 | 7/2014 | Liu et al. |
| 2015/0198583 A1 | 7/2015 | Batra |
| 2015/0306233 A1 | 10/2015 | Chiou et al. |
| 2015/0352213 A1 | 12/2015 | Chou et al. |

FOREIGN PATENT DOCUMENTS

| | | |
|---|---|---|
| CN | 1943606 | 4/2007 |
| CN | 102579434 | 7/2012 |
| CN | 105030760 | 11/2015 |
| CN | 105267205 | 1/2016 |
| EP | 2 952 184 | 12/2015 |
| JP | 2006117663 | 5/2006 |
| JP | 2012144512 | 8/2012 |
| JP | 2014143995 | 8/2014 |
| JP | 2015229675 | 12/2015 |
| TW | 201106947 | 3/2011 |
| WO | 2005/082407 | 9/2005 |
| WO | 2007036074 | 4/2007 |

OTHER PUBLICATIONS

Adjuvant therapy: Treatment to keep cancer from returning (https://www.mayoclinic.org/diseases-conditions/cancer/in-depth/adjuvant-therapy/art-20046687, Apr. 2, 2015) (Year: 2015).*
Bobustuc et al. (Pancreas, 44, 626-635, May 2015) (Year: 2015).*
Pang et al. (Food and Chemical Toxicology, 2013, 59, 281-288; NPL document 1 of IDS filed Apr. 15, 2019) (Year: 2013).*
Yu et al. (Int J Biochem Cell Biol, 2012, 44, 2144-2151) (Year: 2012).*
Asiedu, M.K. et al., "AXL induces epithelial-to-mesenchymal transition and regulates the function of breast cancer stem cells", Oncogene, 2014, vol. 33(10), pp. 1316-1324.
Yu, Y.L. et al., "Extended O6-methylguanine methyltransferase promoter hypermethylation following n-butylidenephthalide combined with 1,3-bis(2-chloroethyl)-1-nitrosourea (BCNU) on inhibition of human hepatocellular carcinoma cell growth", Journal of Agricultural and Food Chemistry, 2010, vol. 58(3), pp. 1630-1638.
Kan, W.L.T. et al., "Study of the anti-proliferative effects and synergy of phthalides from Angelica sinensis on colon cancer cells", Journal of Ethnopharmacology, 2008, vol. 120(1), pp. 36-43.
Wei, C.W. et al., "n-Butylidenephthalide induced apoptosis in the A549 human lung adenocarcinoma cell line by coupled down-regulation of AP-2α and telomerase activity", Acta Pharmacologica Sinica, 2009, vol. 30(9), pp. 1297-1306.
Pang, C.Y. et al., "Proteomic-based identification of multiple pathways underlying n-butylidenephthalide-induced apoptosis in LNCaP human prostate cancer cells", Food and Chemical Toxicology, 2013, vol. 59, pp. 281-288.
Sertel, S. et al., "Chemical Composition and antiproliferative activity of essential oil from the leaves of a medicinal herb, *Levisticum officinale*, against UMSCC1 head and neck squamous carcinoma cells", Anticancer Research, 2011, vol. 31(1), pp. 185-191.
Liu, P.Y. et al., "Expression of Nur77 induced by an n-butylidenephthalide derivative promotes apoptosis and inhibits cell growth in oral squamous cell carcinoma", Invest New Drugs, 2012, vol. 30(1), pp. 79-89.

(Continued)

*Primary Examiner* — Yevgeny Valenrod
(74) *Attorney, Agent, or Firm* — Ping Wang; Morris, Manning & Martin LLP (57) ABSTRACT

A method for decreasing the incidence rate and/or recurrent rate of cancer is provided. The method comprises administering to a subject in need an effective amount of butylidenephthalide (BP).

11 Claims, 5 Drawing Sheets

(56) References Cited

OTHER PUBLICATIONS

Chang, C. Y. et al., "N-butylidenephthalide attenuates Alzheimer's disease-like cytopathy in Down syndrome induced pluripotent stem cell-derived neurons", Scientific Report, 2015, vol. 5:8744, pp. 1-7.
Adjuvant therapy: Treatment to keep cancer from returning (https://www.mayclinic.org/diseases-conditions/cancer/in- dept/adjuvant-therapy/art-20046687, Apr. 2, 2015). (Year: 2015).
File history of U.S. Appl. No. 15/232,262, filed Aug. 9, 2016.
U.S. Appl. No. 15/232,262, filed Aug. 9, 2016, pending.
U.S. Appl. No. 16/025,764, filed Jul. 2, 2018, Pending.
Pang, C.Y. et al., "Proteomic-based identification of multiple pathways underlying n-butylidenephthalide-induced apoptosis in LNCaP human prostate cancer cells", Food and Chemical Toxicology, Aug. 31, 2013, vol. 59, pp. 281-288.
Extended European Search Report dated Mar. 6, 2019 in European Application No. 16836466.9.

\* cited by examiner

USES OF BUTYLIDENEPHTHALIDE

This application is a continuation-in part of U.S. application Ser. No. 15/232,262, filed on Aug. 9, 2016, which claims priority to U.S. Provisional Application Ser. No. 62/207,226 filed on Aug. 19, 2015, in the United States Patent and Trademark Office, and to Taiwan Patent Application No. 105117580 filed on Jun. 3, 2016, in the Taiwan Intellectual Property Office, the disclosures of which are incorporated herein in their entirety by reference.

FIELD

The present invention relates to the use of butylidenephthalide (BP) in decreasing the incidence rate and/or recurrent rate of cancer, and particularly to the use of BP in preventing, mitigating and/or inhibiting of the growth, migration and/or invasion of cancer stem cells (CSCs). The cancer stem cells (CSCs) include oral cancer stem cells, nasopharyngeal cancer stem cells, esophageal cancer stem cells, myeloma stem cells, skin cancer stem cells, melanoma stem cells, thyroid cancer stem cells, lymphoma stem cells, leukemia stem cells, breast cancer stem cells, bladder cancer stem cells, ovarian cancer stem cells, cervical cancer stem cells, prostate cancer stem cells, gastric cancer stem cells, liver cancer stem cells, lung cancer stem cells, colon cancer stem cells, rectal cancer stem cells, pancreatic cancer stem cells, gall bladder cancer stem cells, renal cancer stem cells, thymic carcinoma stem cells and rhabdomyosarcoma stem cells, and especially oral cancer stem cells and pancreatic cancer stem cells.

BACKGROUND

In medicine, a tumor refers to an abnormal cytopathic effect, which is caused by a reaction of various carcinogenic factors that causes cells in the local body tissues to lose normal growth regulation at the genetic level and results in an abnormal cell proliferation. Those abnormal proliferated cells will aggregate into a mass, and this is called as a "tumor." "Cancer" is the most common type of tumor. The abnormal proliferated "cancer cells" will not only aggregate into a mass, but also spread and metastasize to other tissues or organs. Therefore, cancer is also known as a malignant tumor. The proliferation and metastasis of cancer cells will cause severe abnormalities of physiological function and is very difficult to cure; therefore, cancer is currently the first cause of death worldwide.

Traditional methods for treating cancer include surgery, chemotherapy and radiation therapy, etc. Cancer, however, cannot be cured completely by surgical excision of the mass because the cancer cells not exactly cut off may continuously grow and result in an exacerbation of the patient's condition. Therefore, surgical excision is not used alone in the therapy for cancer, and is usually combined with other therapeutic methods such as chemotherapy and/or radiation therapy. In chemotherapy, chemical drugs (such as an alkylating agent) are used to kill the cancer cells having a high proliferation rate. However, most chemical drugs used in chemotherapies also act on normal cells, resulting in severe side effects (include vomiting, alopecia, fatigue, bleeding, anemia, etc.) to cancer patients. Radiation therapy (e.g., gamma knife radiosurgery) breaks down the DNA of cancer cells on the principle that rapidly dividing cancer cells are more sensitive to radiation than normal cells. However, when high-energy radiation destroys cancer cells, normal cells may also be radiated simultaneously, resulting in side effects such as a loss of leukocytes, fatigue, insomnia, pain, and poor appetite. Furthermore, chemotherapy and radiation therapy are not effective for a part of cancer patients in the late stages.

Research has shown that most cancer cells do not have the ability to induce a tumor and only few cancer cells have tumorigenicity. Those cancer cells with tumorigenicity have characteristics of stem cells (i.e., have the ability of self-renewal and differentiation), and can continuously grow and differentiate into different kinds or types of tumor cells, and thus, are called as "cancer stem cells (CSCs)" or "tumor stem cells". Research has also shown that cancer stem cells have the potential to form a tumor and develop into cancer. In particular, cancer stem cells will develop into other kinds of cancer when metastasizing to other tissues or organs of the body. Furthermore, in the tissues of such as leukemia, breast cancer, brain cancer, ovarian cancer, prostate cancer, colon cancer, rectal cancer, or oral cancer, cancer stem cells are more resistant to chemotherapy or radiation therapy than other cells. Such resistance is highly correlated with the recurrence, invasion, and metastasis of the tumor and survival rate of the patient. Thus, if the growth, migration, invasion and/or metastasis of cancer stem cells can be prevented, mitigated or inhibited effectively, the success rate for treating the tumor and cancer and the survival rate of patient can be improved.

Currently, the therapeutic methods (including surgery, chemotherapy and radiation therapy, etc.) for preventing, mitigating or inhibiting the growth, migration, invasion or metastasis of cancer stem cells in clinic are all inefficient. Therefore, there is a necessity and urgency for developing a method or a drug for preventing, mitigating or inhibiting the growth, migration, invasion or metastasis of cancer stem cells effectively to decrease the incidence rate, recurrent rate, and death rate, as well as to improve the cure rate and reduce side effects.

Inventors of the present invention found that BP is effective in inhibiting the expressions of the stemness factors of cancer stem cells, especially in inhibiting the expressions of Sox-2 and Oct4, and thus, can inhibit the growth, migration and invasion of cancer stem cells and can be used to provide a medicament, a food product or a food additive for decreasing the incidence rate and/or recurrent rate of cancer.

SUMMARY

An objective of the present invention is to provide a use of butylidenephthalide (BP) in the manufacture of a preparation, wherein the preparation is for decreasing the incidence rate and/or recurrent rate of cancer. Preferably, the preparation is a medicament, a food product, or a food additive for preventing, mitigating and/or inhibiting the growth, migration and/or invasion of cancer stem cells (CSCs).

Another objective of the present invention is to provide a method for decreasing the incidence rate and/or recurrent rate of cancer, comprising administering to a subject in need an effective amount of butylidenephthalide (BP). Preferably, the method is for preventing, mitigating and/or inhibiting the growth, migration and/or invasion of cancer stem cell (CSC). More preferably, in the method of the present invention, BP is administered in an amount that is sufficient to inhibit the expressions of Sox-2 and Oct4, thereby preventing, mitigating and/or inhibiting the growth, migration and/or invasion of cancer stem cell (CSC).

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

The patent application contains at least one drawing executed in color. Copies of this patent document with color drawing(s) will be provided by the Patent and Trademark Office upon request and payment of the necessary fee.

FIG. 5 shows the results of transwell invasion assay system, showing the invasion ability of HINC-TIC-like oral stem cells (i.e., ALDH1$^+$CD44$^+$-1 cell line or ALDH1$^+$CD44$^+$-2 cell line) treated with different concentrations of BP, wherein

FIG. 6 shows the results of a soft agar colony formation assay, showing the colony-forming ability of oral cancer stem cells treated with different concentrations of BP, wherein

FIG. 7 shows the results of an animal experiment, showing the ability of 13' to inhibit the tumor initiating activity of cancer stem cells, including the results of the mice without BP treatment (i.e., "control group," ), the mice treated with 100 mg/kg of BP (i.e., "100 mg/kg group," ), and the mice treated with 200 mg/kg of BP (i.e., "200 mg/kg group," ), wherein

DETAILED DESCRIPTION

The following will describe some of the embodiments of the present invention in detail. However, without departing from the spirit of the present invention, the present invention may be embodied in various embodiments and should not be limited to the embodiments described in the specification. In addition, unless otherwise indicated herein, the expressions "a," "an", "the", or the like recited in the specification of the present invention (especially in the claims) are intended to include the singular and plural forms. The term "effective amount" or "therapeutically effective amount" used in the specification refers to the amount of compound that can at least partially alleviate the condition that is being treated in a suspected subject when administrated to the subject in need. The term "subject" used in this specification refers to a mammalian, including human or non-human animals.

Inventors of the present invention found that butylidenephthalide (BP) is effective in inhibiting the viability of cancer stem cells, inhibiting the expressions of the stemness-maintenance markers (e.g., CD133, Sox-2, Oct4) of cancer stem cells and inhibiting the migration ability of cancer stem cells. In some embodiments of the present invention, BP prevented, mitigated and/or inhibited the growth, migration and/or invasion of cancer stem cells by inhibiting the expressions of Sox-2 and Oct-4.

Therefore, the present invention relates to the use of BP in the manufacture of a preparation, wherein the preparation is for decreasing the incidence rate and/or recurrent rate of cancer, particularly for preventing, mitigating and/or inhibiting the growth, migration and/or invasion of cancer stem cells.

The preparation of the present invention can be used in any suitable cancer stem cells and the examples of the cancer stem cells include, for example, oral cancer stem cells, nasopharyngeal cancer stem cells, esophageal cancer stem cells, myeloma stem cells, skin cancer stem cells, melanoma stem cells, thyroid cancer stem cells, lymphoma stem cells, leukemia stem cells, breast cancer stem cells, bladder cancer stem cells, ovarian cancer stem cells, cervical cancer stem cells, prostate cancer stem cells, gastric cancer stem cells, liver cancer stem cells, lung cancer stem cells, colon cancer stem cells, rectal cancer stem cells, pancreatic cancer stem cells, gall bladder cancer stem cells, renal cancer stem cells, thymic carcinoma stem cells and rhabdomyosarcoma stem cells. In some embodiments of the present invention, the preparation is used to prevent, mitigate and/or inhibit the growth, migration and/or invasion of oral cancer stem cells and/or pancreatic cancer stem.

The preparation in accordance with the present invention can be provided in any suitable form without particular limitations. For example, the preparation can be provided as medicaments, but is not limited thereby. The preparation can also be provided in liquid or solid form as a food product or food additive.

When the preparation according to the present invention is provided as a medicament, the medicament can be prepared in any suitable dosage form depending on the desired administration manner. For example, the medicament can be administered by oral or parenteral (e.g., subcutaneous, intravenous, intramuscular, peritoneal, or nasal) route to a subject in need, but is not limited thereby. Depending on the form and purpose, suitable carriers can be chosen and used to provide the medicament, wherein examples of the suitable carriers include excipients, diluents, auxiliaries, stabilizers, absorbent retarders, disintegrants, hydrotropic agents, emulsifiers, antioxidants, adhesives, binders, tackifiers, dispersants, suspending agents, lubricants, hygroscopic agents, etc.

As a dosage form suitable for oral administration, the medicament provided by the present invention can comprise any pharmaceutically acceptable carrier (e.g., water, saline, dextrose, glycerol, ethanol or its analogs, cellulose, starch, sugar bentonite, or combinations thereof) that will not adversely affect the desired effects of BP. The medicament can be provided in any dosage form suitable for oral administration, such as be provided as a tablet (e.g., dragee), a pill, a capsule, a granule, a pulvis, a fluid extract, a solution, syrup, a suspension, an emulsion, and a tincture, etc.

As for an injection form for subcutaneous, intravenous, intramuscular, or peritoneal administration or a drip form, the medicament provided by the present invention can comprise one or more ingredient(s) such as an isotonic solution, a salt-buffered saline (e.g., phosphate-buffered saline or citrate-buffered saline), a hydrotropic agent, an emulsifier, 5% sugar solution, and other carriers to provide the medicament as an intravenous infusion, an emulsified intravenous infusion, a powder for injection, a suspension for injection, or a powder suspension for injection, etc. Alternatively, the medicament can be prepared as a pre-injection solid. The pre-injection solid can be provided in a form which is soluble in other solutions or suspensions, or in an emulsifiable form. A desired injection is provided by dissolving the pre-injection solid in a solution or a suspension or emulsifying it prior to being administered to a subject in need. In addition, examples of the dosage form for external use which are suitable for nasal or transdermal administration include an emulsion, a cream, gel (e.g., hydrogel), paste (e.g., a dispersion paste, an ointment), a spray, or a solution (e.g., a lotion, a suspension).

Optionally, the medicament provided by the present invention can further comprise a suitable amount of additives, such as a flavoring agent, a toner, or a coloring agent for enhancing the palatability and the visual perception of the medicament, and/or a buffer, a conservative, a preservative, an antibacterial agent, or an antifungal agent for improving the stability and storability of the medicament. In addition, the medicament can optionally further comprise one or more other active ingredients or be used in combination with a medicament comprising one or more other active ingredients, to further enhance the effects of the medicament or to increase the application flexibility and adaptability of the formulation thus provided, as long as the other active ingredient(s) will not adversely affect the desired effects of BP.

Depending on the age, body weight, and health conditions (such as the disease to be treated and its severity) of the subject to be administrated, the medicament provided by the present invention can be applied with various administration frequencies, such as once a day, multiple times a day, or once every few days, etc. For example, when the medicament is applied orally to a subject for decreasing the incidence rate and/or recurrent rate of cancer, the dosage of the medicament is about 30 mg (as BP)/kg-body weight to about 500 mg (as BP)/kg-body weight per day, preferably about 40 mg (as BP)/kg-body weight to about 120 mg (as BP)/kg-body weight per day, and more preferably about 50 mg (as BP)/kg-body weight to about 90 mg (as BP)/kg-body weight per day, wherein the unit "mg/kg-body weight" refers to the dosage required per kg-body weight of the subject. However, for acute patients, the dosage may be optionally increased up to such as several folds or dozen fold, depending on the practical requirements.

Optionally, the medicament of the present invention can be used in combination with surgery, chemotherapy, radiation therapy, antibody therapy, immunotherapy, anti-angiogenesis therapy, phenotype conversion and/or differentiation therapy, to decrease the recurrent rate of cancer.

When the preparation according to the present invention is provided as a food additive, the food additive can be in a form that could be conveniently added during the food manufacturing processes, such as in the form of powder, liquid, suspension or granule. When the preparation according to the present invention is provided as a food product, the food product can be such as milk products, processed meat, breads, pasta products, biscuits, troches, juices, teas, sport drinks, nutritious drinks, and the likes, and can be heath food (e.g., nutritional supplements after surgery), but is not limited thereby.

Depending on the age, body weight and healthy conditions of the subject to be administrated, the health food provided by the present invention can be taken in various frequencies, such as once a day, several times a day or once every few days, etc. The amount of BP in the health food provided by the present invention can be adjusted, preferably to the amount that should be taken daily, depending on the specific population. For example, if the recommended daily dosage for a subject is about 50 mg and each serving of the health food contains 25 mg of BP, the subject can take about two servings of the health food per day.

The recommended daily dosages, use standards and use conditions for a specific population (e.g., pregnant woman and diabetic patients), or recommendations for a use in combination with another food or medicament can be indicated on the outer package of the health food of the present invention, and thus, is favorable for user to take the health food by him- or herself safely and securely without the instructions of a doctor, pharmacist, or related executive.

The present invention also provides a method for decreasing the incidence rate and/or recurrent rate of cancer, comprising administering to a subject in need an effective amount of butylidenephthalide (BP). In this method, the applied form and suitable dosage of BP and suitable cancer stem cells are all in line with the above description about the preparation of the present invention.

The present invention will be further illustrated in detail with specific examples as follows. However, the following examples are provided only for illustrating the present invention, and the scope of the present invention is not limited thereby. The scope of the present invention is shown in the claims.

EXAMPLES

Example 1: Effect of BP on Inhibiting the Growth of Cancer Stem Cells

To investigate the effect of BP on inhibiting the growth of cancer stem cells, NHOKs (normal human oral keratinocytes) and HNC-TIC (head and neck cancer-derived tumor initiating cell)-like oral stem cells (i.e., ALDH1$^+$CD44$^+$-1 cell line or ALDH1$^+$CD44$^+$-2 cell line) were treated with different concentrations (0, 25, 50 and 100 μg/ml) of BP for 24 hours, and then, an MTT assay was utilized to analyzed the viabilities of NHOKs and HNC-TIC-like oral stem cells (i.e., ALDH1$^+$CD44$^+$-1 cell line and ALDH1$^+$CD44$^+$-2 cell line). The results are shown in FIG. 1.

Figure 1:
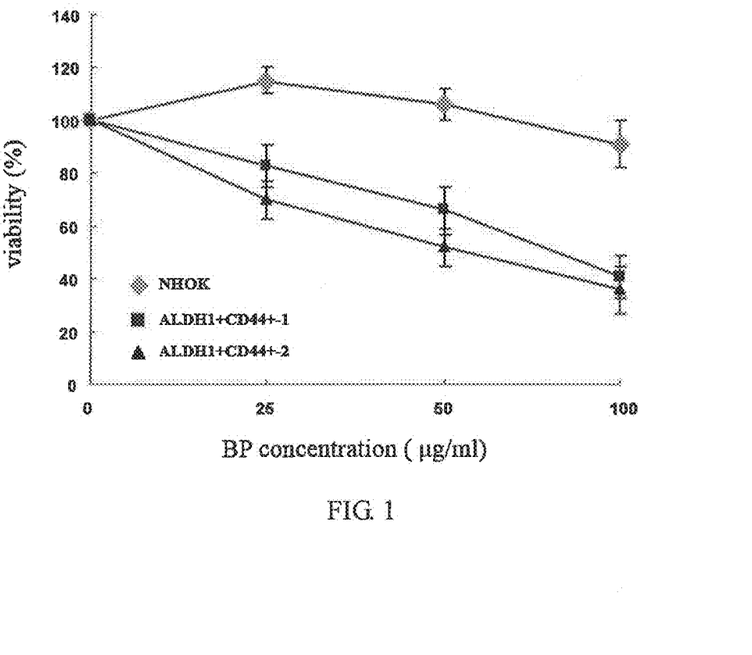
FIG. 1 is a curve diagram showing the relative viability of NHOKs (normal human oral keratinocytes ) treated with different concentrations of BP and that of HNC-TIC (head and neck cancer-derived tumor initiating cell)-like oral stem cells (i.e., ALDH1$^+$CD44$^+$-1 cell line or ALDH1$^+$CD44$^+$-2 cell line ) treated with different concentrations of BP.

As shown in FIG. 1, the viability of NHOKs did not decrease along with the increment in the concentration of BP, while that of HNC-TIC-like oral stem cells (i.e., ALDH1$^+$CD44$^+$-1 cell line and ALDH1$^+$CD44$^+$-2 cell line) decreased along with the increment in the concentration of BP. These results indicate that BP is effective in inhibiting the growth of cancer stem cells and has no cytotoxicity to normal cells. Therefore, BP will not cause cytotoxicity-induced side effects and thus can be used to provide a quality drug for inhibiting the growth of cancer stem cells.

Example 2: Effect of BP on Inhibiting the Stemness of Cancer Cells and Cancer Stem Cells (2-1)

Figure 2:
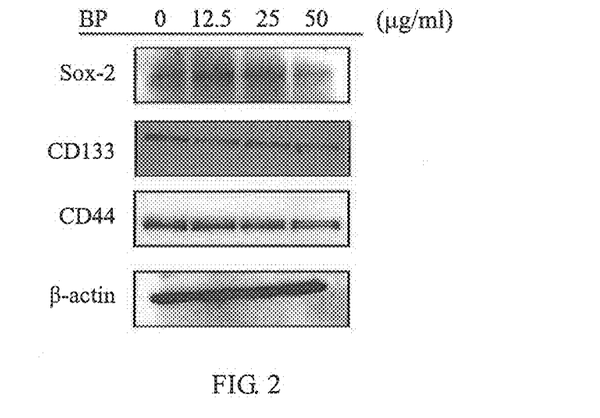
FIG. 2 is a photograph of the results of Western blotting, showing the protein expressions of Sox-2, CD133, CD44 and β-actin in MiaPaCa-2 cells (i.e., a cell line of pancreatic cancer cells) treated with different concentrations of BP.

It has been known that CD44, CD133, Sox-2 (sex-determining region Y protein (SRY)-related high-mobility group box 2) and Oct4 (octamerbinding transcription factor 4) proteins all are stemness-maintenance markers of cancer stem cells and participate in the regulation of the self-renewal and differentiation of cancer stem cells. MiaPaCa-2 cell line (i.e., a cell line of pancreatic cancer cells) was treated with different concentrations (0, 12.5, 25, and 50 µg/ml) of BP for 24 hours, and then, proteins were extracted from the cells to conduct Western blotting to determine the expressions of Sox-2, CD133 and CD44 proteins in the BP-treated MiaPaCa-2 cells. The results are shown in FIG. 2. Yet another. HNC-TIC-like oral stem cells (i.e., ALDH1$^+$CD44$^+$-1 cell line or ALDH1$^+$CD44$^+$-2 cell line) were treated with different concentrations (0, 12.5, 25, and 50 µg/ml) of BP for 24 hours, and then, proteins were extracted from the cells to conduct Western blotting to determine the expressions of Sox-2 and Oct4 proteins in the BP-treated HNC-TIC-like oral stem cells (i.e., ALDH1$^+$CD44$^+$-1 cell line and ALDH1$^+$CD44$^+$-2 cell line). The results are shown in FIG. 3.

Figure 3:
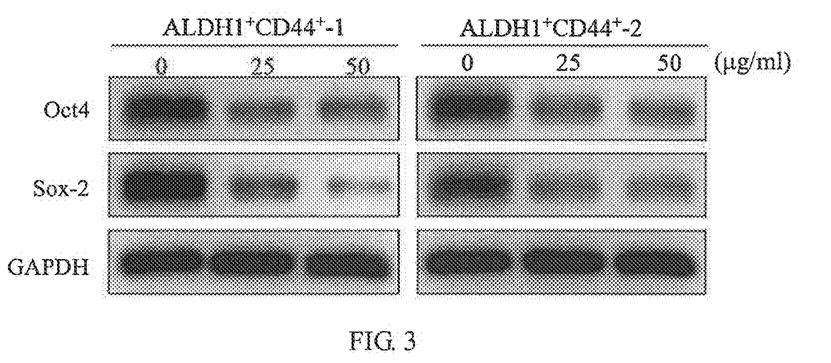
FIG. 3 is a photograph of the results of Western blotting, showing the protein expressions of Oct4, Sox-2 and GAPDH in HNC-TIC-like oral stem cells (i.e., ALDH1$^+$CD44$^+$-1 cell line or ALDH1$^+$CD44$^+$-2 cell line) treated with different concentrations of BP.

As shown in FIG. 2, the expressions of Sox-2, CD133 and CD44 proteins in MiaPaCa-2 cells significantly decreased along with the increment in the concentration of BP, As shown in FIG. 3, the expressions of Sox-2 and Oct4 proteins in the HNC-TIC-like oral stem cells (i.e., ALDH1$^+$CD44$^+$-1 cell line and ALDH1$^+$CD44-2 cell line) significantly decreased along with the increment in the concentration of BP. These results indicate that BP is effective in inhibiting the stemness of cancer cells and cancer stem cells.

(2-2)

ALDH protein is also an important stemness-maintenance marker of cancer stem cells and participates in the regulation of the self-renewal and differentiation of cancer stem cells. HNC-TIC-like oral stem cells (i.e., ALDH1$^+$CD44$^+$-1 cell line or ALDH1$^+$CD44$^+$-2 cell line) were treated with different concentrations (0, 25 and 50 µg/ml) of BP for 24 hours, and then, 1×10$^5$ cells obtained from each group were separately suspended in 50 µl of a stem cell detection kit (i.e., ALDEEFLUOR array kit, purchased from STEMCELL Technologies Inc., Vancouver, Canada) buffer and the cell suspension of each group was separately added with ALDE-FLUOR to a final concentration of 1 µM. Thereafter, a sample of each group was stained by 7-ADD and then analyzed by flow cytometry analysis to determine the ALDH activity of HNC-TIC-like oral stem cells (i.e., ALDH1$^+$CD44$^+$-1 cell line and ALDH1$^+$CD44$^+$-2 cell line). The results are shown in FIG. 4.

The above experimental procedure was repeated, but the cell suspension of each group was further added with N,N-diethylaminobenzaldehyde (DEAB, i.e., an inhibitor of ALDH) to a final concentration of 150 µM of DEAB separately. The results are also shown in FIG. 4.

Figure 4:
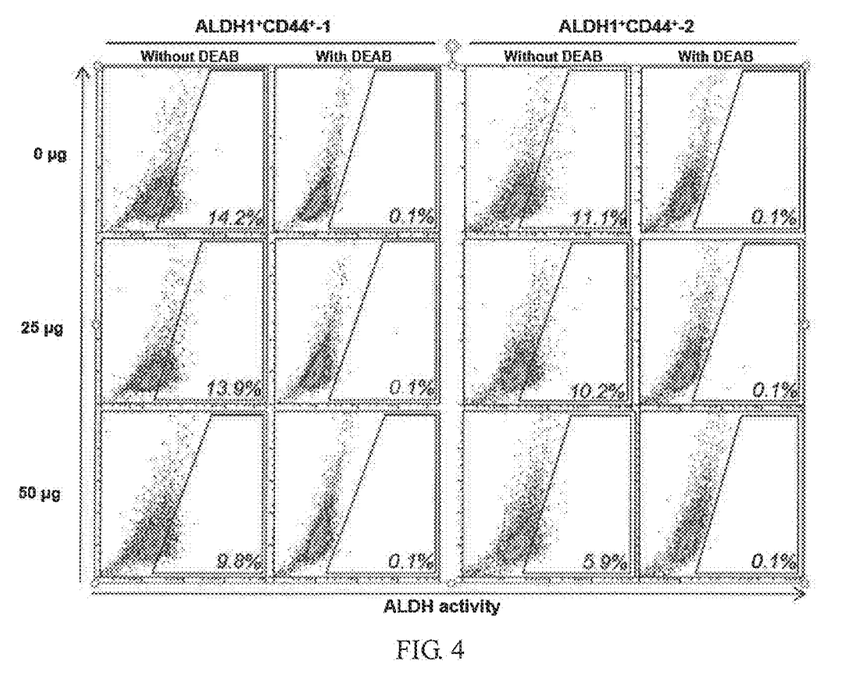
FIG. 4 shows the results of flow cytometry analysis, showing the ALDH activity of HNC-TIC-like oral stem cells (i.e., ALDH1$^+$CD44$^+$-1 cell line or ALDH1 CD44$^+$-2 cell line) treated with different concentrations of BP in the presence or absence of N,N-diethylaminobenzaldehyde (DEAB)

As shown in FIG. 4, in the DEAB-added group, no matter there was a treatment of BP or not, the live cells with ALDH activity were only 0.1% of total live cells. On the other hand, in the group without DEAB addition, the number of live cells with ALDH activity increased along with the increment in the concentration of BP. These results indicate that BP is effective in inhibiting the ALDH activity of cancer stem cells, and prove again that BP is effective in inhibiting stemness of cancer stem cells.

Figure 5A:
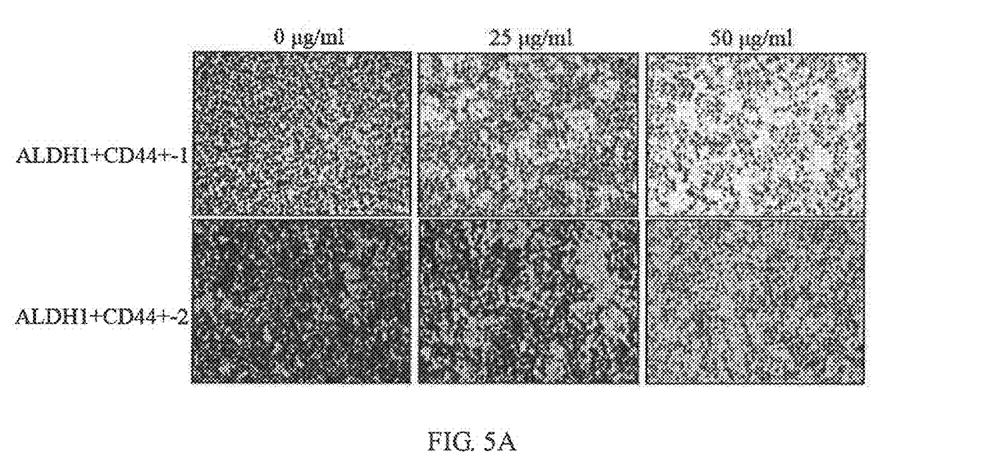
FIG. 5A is a photograph showing the staining results of the polycarbonate filter membrane in the lower chamber.
Figure 5B:
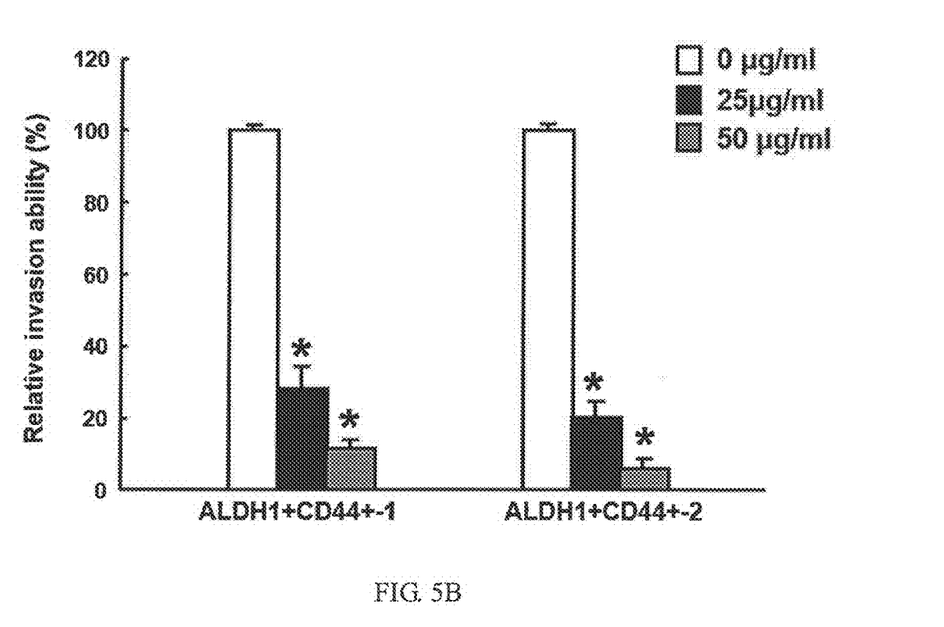
FIG. 5B is a bar diagram showing the quantified results of relative invasion ability.

Example 3: Effect of BP on Inhibiting the Migration and Invasion of Cancer Stem Cells In this research, the effect of BP on inhibiting the migration and invasion of cancer stem cells was investigated by a transwell invasion assay system (i.e., Transwell® system, purchased from Corning, UK) with a polycarbonate filter membrane of 8-µm pore size (purchased from Corning, UK). First, the polycarbonate filter membrane was coated with Matrigel™ (purchased from BD Pharmingen, USA), and then, the coated membrane was placed in the lower chamber of the transwell invasion assay system. Then, the lower chamber was filled with 10% serum-containing medium. On the other hand, HNC-TIC-like oral stem cells (i.e., ALDH1$^+$CD44$^+$-1 cell line or ALDH1$^+$CD44$^+$-2 cell line) were treated with different concentrations (0, 25 and 50 µg/ml) of BP for 24 hours, and then, the treated cells of each group was cultured in the upper chamber which was filled with serum-free medium, at a cell density of 1×10 cells/100 µl for 24 hours. Lastly, the medium of the lower chamber was removed, and the polycarbonate filter membrane in the lower chamber was taken out, fixed with 4% formalin and stained with crystal violet. The invasion cancer cells of each group were counted and photographed over five visual fields of the membrane with the use of a 100-fold magnification under a microscope. The results are shown in FIG. 5A. The relative invasion ability of cells of each experimental group was calculated based on the result of the group treated with 0 µg/ml of BP. The results are shown in FIG. 5B.

As shown in FIG. 5A, the number of cells on the polycarbonate filter membrane significantly reduced along with the increment in the concentration of BP. As shown in FIG. 5B, the relative invasion ability of cancer stem cells also decreased along with the increment in the concentration of BP. These results indicate that BP is effective in inhibiting the migration and invasion of cancer stem cells.

Example 4: Effect of BP on Inhibiting the Tumor Initiating Activity of Cancer Stem Cells (4-1)

Figure 6A:
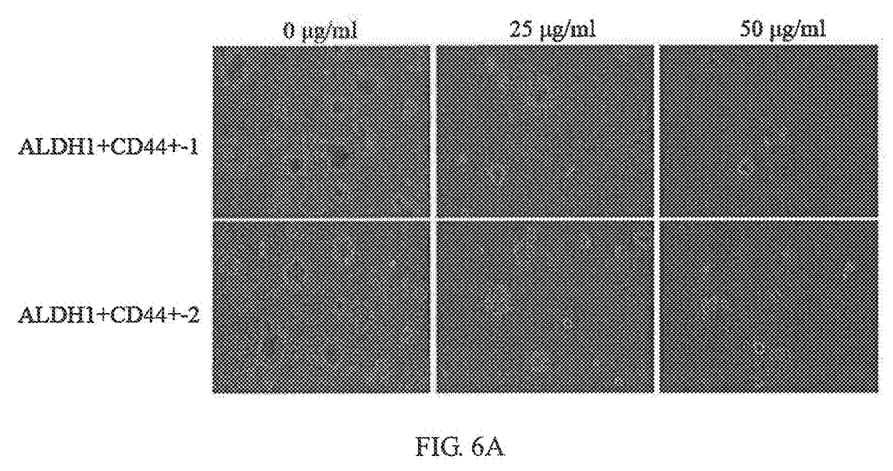
FIG. 6A is a photograph showing the colony formation of ALDH1$^+$CD44$^+$-1 cell line and ALDH1$^+$CD44$^+$-2 cell line.
Figure 6B:
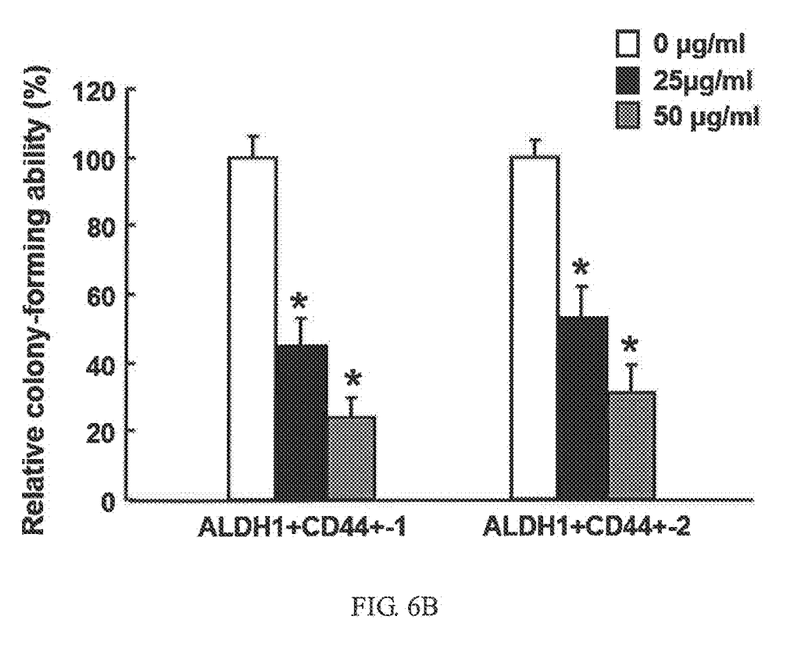
FIG. 6B is a bar diagram showing the relative colony-forming ability of ALDH1$^+$CD4$^+$-1 cell line and ALDH1$^+$CD44$^+$-2 cell line.

In this research, a soft agar colony formation assay was used to investigate the effect of BP on inhibiting the tumor initiating activity of cancer stem cells. First, HNC-TIC-like oral stem cells (i.e., ALDH1$^+$CD44$^+$-1 cell line or ALDH1$^+$CD44$^+$-2 cell line) were treated with different concentrations (0, 25 and 50 µg/ml) of BP for 24 hours, and then, the treated cells of each group was separately seeded in the top agar [containing DMEM (Dulbecco's Modified Eagle's Medium medium), 10% (v/v) Fetal Calf Serum (FCS) and 0.3% (w/v) agar] (purchased from Sigma-Aldrich) at an initial cell number of 2×10$^4$. On the other hand, a six-well culture dish was coated with the bottom agar [containing DMEM, 10% (v/v) FCS and 0.6% (w/v) agar](purchased from Sigma-Aldrich), 2 ml for each well. After the bottom agar was solidified, each group of the top agar (containing oral cancer stem cells) was respectively added onto the bottom agar in different wells of the dish, 2 ml for each well. Thereafter, the culture dish was placed in an 37° C. incubator for 4 weeks. Lastly, the bottom agar was stained with 0.005% crystal violet, the number of colonies (with a diameter ≥100 µm) was counted over five fields per well with the use of a microscope, and those fields were photographed. The results are shown in FIG. 6A. The relative colony-forming ability of cells of each experimental group was calculated based on the result of the group treated with 0 μg/ml of BP. The results are shown in FIG. 6B.

As shown in FIG. 6A, the number of colonies in the bottom agar significantly decreased along with the increment in the concentration of BP. As shown in 6B, the relative colony-forming ability of cancer stem cells also decreased along with the increment in the concentration of BP. These results indicate that BP is effective in inhibiting the tumor initiating activity of cancer stem cells.

(4-2)

Figure 7A:
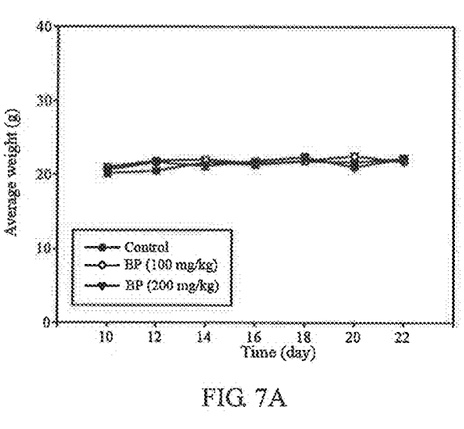
FIG. 7A shows the average weight (g) of each group of mice over a period of time.
Figure 7B:
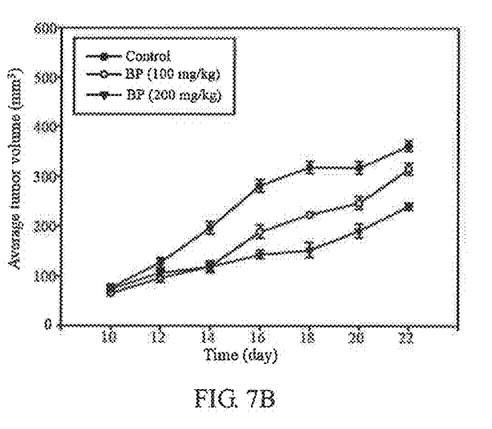
FIG. 7B shows the average tumor volume (mm$^3$) of each group of mice over a period of time.
Figure 7C:
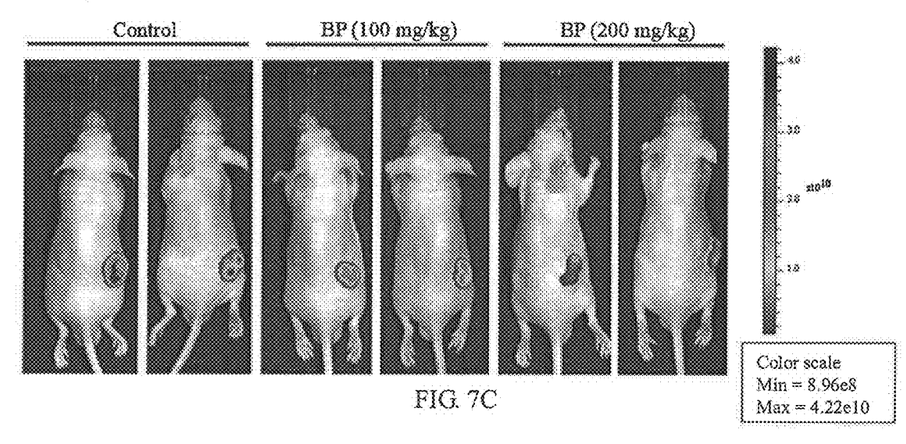
FIG. 7C is a photograph showing the GFP intensity (i.e. green fluorescence) in each group of mice, and FIG. 7D) is a bar diagram showing the GFP intensity in each group of mice.
Figure 7D:
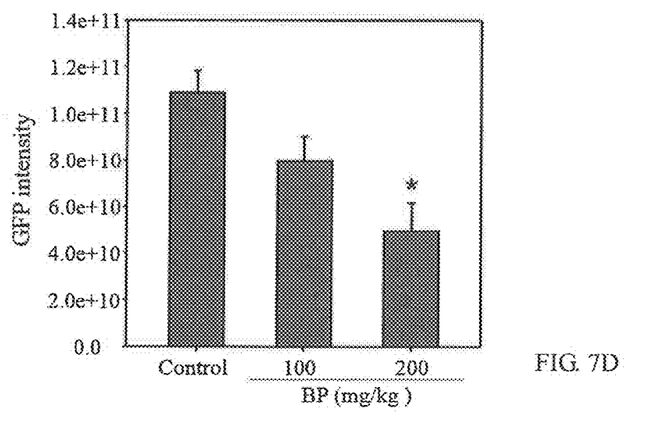

In this research, the effect of BP on inhibiting the tumor initiating activity of cancer stem cells was further investigated by animal experiments. First, 5-6 weeks old BALB/c nu/nu mice (weight 18-22 g) were bred under the same condition for 4 weeks. Then, HNC-TIC-like oral stem cells stably transfected with GFP-tagged constructs were injected ($1 \times 10^4$ cells/0.1 mL/mouse) subcutaneously into the axilla of mice. After tumors reached 100 mm$^3$, mice were grouped into one control group and two experimental groups (three groups in total, n=3 per group). Then, one experimental group was injected daily with 100 mg/kg of BP for 6 days and another experimental group was injected daily with 200 mg/kg of BP for 6 days. The control group was injected daily with a vehicle (without BP) for 6 days. Ten days after the injection of BP or vehicle, the length and width were measured every 2 days (22 days in total), and then, the average tumor volume was calculated according to the following Formula 1. The results are shown in FIGS. 7A and 7B. At the same time, the GFP signal (i.e., green fluorescence) of each group was detected and photographed by the IVIS Imaging system. The results are shown in FIG. 7C. The GFP intensity of each group was analyzed by Image-Pro Plus software. The results are shown in FIG. 7D.

[length×width$^2$]/2 (unit: mm$^3$)  Formula 1:

As shown in FIGS. 7A to 7D, under the condition that the body weight of mice didn't change significantly, as compared to the control group without BP injection, the GFP intensity of the two experimental groups significantly decreased, and the tumor volume of the two experimental groups decreased over a period of time after the BP injection. These results indicate again that BP is effective in inhibiting the tumor initiating activity of cancer stem cells.

As shown by the above experimental results, BP is effective in inhibiting the viabilities of cancer stem cells, inhibiting the expressions of the stemness-maintenance markers of cancer stem cells, and inhibiting the migration ability of cancer stem cells. In particular, BP is effective in inhibiting the expressions of Sox-2 and Oct4, and thus, can be used to decrease the incidence rate and/or recurrent rate of cancer by preventing, mitigating and/or inhibiting the growth, migration and/or invasion of cancer stem cells.

What is claimed is:

1. A method for decreasing the recurrent rate of cancer, comprising administering an effective amount of butylidenephthalide (BP) to a subject that has undergone a cancer therapy and has completed the cancer therapy.

2. The method as claimed in claim 1, wherein the method is for preventing, mitigating and/or inhibiting the growth, migration and/or invasion of cancer stem cell (CSC).

3. The method as claimed in claim 2, wherein BP is administered in an amount that is sufficient to inhibit the expressions of Sox-2 and Oct4, thereby preventing, mitigating and/or inhibiting the growth, migration and/or invasion of cancer stem cell (CSC).

4. The method as claimed in claim 2, wherein the cancer stem cell (CSC) is at least one of oral cancer stem cells, nasopharyngeal cancer stem cells, esophageal cancer stem cells, myeloma stem cells, skin cancer stem cells, melanoma stem cells, thyroid cancer stem cells, lymphoma stem cells, leukemia stem cells, breast cancer stem cells, bladder cancer stem cells, ovarian cancer stem cells, cervical cancer stem cells, prostate cancer stem cells, gastric cancer stem cells, liver cancer stem cells, lung cancer stem cells, colon cancer stem cells, rectal cancer stem cells, pancreatic cancer stem cells, gall bladder cancer stem cells, renal cancer stem cells, thymic carcinoma stem cells and rhabdomyosarcoma stem cells.

5. The method as claimed in claim 2, wherein the cancer stem cell (CSC) is oral cancer stem cell and/or pancreatic cancer stem cell.

6. The method as claimed in claim 2, wherein the cancer stem cell (CSC) is oral cancer stem cell.

7. The method as claimed in claim 2, wherein the cancer stem cell (CSC) is pancreatic cancer stem cell.

8. The method as claimed in claim 1, wherein BP is administered as a medicament, a food product, or a food additive.

9. The method as claimed in claim 1, wherein BP is administered at an amount ranging from about 30 mg/kg-body weight to about 500 mg/kg-body weight per day.

10. The method as claimed in claim 1, wherein BP is administered at an amount ranging from about 40 mg/kg-body weight to about 120 mg/kg-body weight per day.

11. The method as claimed in claim 1, wherein BP is administered at an amount ranging from about 50 mg/kg-body weight to about 90 mg/kg-body weight per day.

* * * * *